United States Patent [19]

Kloepper et al.

[11] Patent Number: 5,503,652
[45] Date of Patent: Apr. 2, 1996

[54] BACTERIAL CULTURES FOR ROOT-COLONIZING PLANTS

[75] Inventors: Joseph W. Kloepper, Georgetown; Catherine Simonson, Mississauga; Ran Lifshitz, Thornhill, all of Canada

[73] Assignee: Cominco Fertilizers, Calgary, Canada

[21] Appl. No.: 438,740

[22] Filed: Jan. 31, 1995

Related U.S. Application Data

[63] Continuation of Ser. No. 942,822, Dec. 17, 1986, abandoned.

[51] Int. Cl.$^6$ .............................. C05F 11/08; H01R 4/10; A01C 1/06
[52] U.S. Cl. .............................. 71/6; 435/850; 435/876; 435/877; 435/880; 435/253.3; 47/57.6; 71/24
[58] Field of Search .................... 71/1, 6, 7, 24; 435/253.3, 850, 876, 877, 880; 47/57.6

[56] References Cited

U.S. PATENT DOCUMENTS 4,584,274  4/1986  Suslow ................................. 435/253

FOREIGN PATENT DOCUMENTS 1172585  8/1984  Canada .
0064720  11/1982  European Pat. Off. .

OTHER PUBLICATIONS

Burr et al, "Beneficial Plant Bacteria", Critical Reviews in Plant Science, 1984 2(1) 1–20 (No Month).
Rao, "Interaction of Nitrogen Fixing . . . Microorganisme" Current Developments in Biologicol Nitrogen Fixation 1984, pp. 37–64.
Lifshitz, et al, Applied and Environmental Microbiology, *Nitrogen–Fixing Pseudomonads Isolated from Roots of Plants Grown in the Canadian High Arctic,* vol. 51, No. 2, 1986, pp. 251–255. No Month.
Grimes, et al., Soil Biol. Biochem. *Influence of Pseudomonas Putida on Nodulation of Phaseolus Vulgaris,* Vol. 16, No. 1, pp. 27–30, 1984. No Month.
Translation of Russian article, "Influence of soil microorganisms on virulence and activity of nodule forming bacteria", (and Russian article). No. Date.
Suslow, et al., *The American Phytopathological Society,* "Rhizo–bacteria of Sugar Beets: Effects of Seed Application and Root Colonization on Yield", vol. 72, No. 2, pp. 199–206, (1982) No Month.
Howell, et al., *Phytopathology,* "Control of Rhizoctonia solani on cotton seedlings with Pseudomonas fluorescens and with an antibiotic produced by the bacterium", 69, pp. 480–482, (1979) No Month.
Kloepper, et al., *Phytopathology,* "Effects of Rhizosphere Colonization by Plant Growth–Promoting Rhizobacteria on Potato Plant Development and Yield", 70, pp. 1078–1082, (1980). No Month.
Peters, et al., *Soil Science,* "Effects of Legume Exudates on the Root Nodule Bacteria", vol. 102, No. 5, pp. 380–387, (1966), No Month.
European Search Report.
N. Sakthivel, et al., *IRRN,* "Bacterization of rice with Pseudomonas fluorescens reduces sheath rot (ShR) infection", 11:3 (Jun, 1986), pp. 17–19.
D. M. Weller, et al., *Canadian Journal of Plant Pathology,* "Increased growth of wheat by seed treatments with fluorescent pseudomonads, and Implications of Pythium control", 1986, vol. 8(3), 228–334. No. Month.
A. Hussain et al., *Folia Microbiol.* (Prague), "Formation of Biologically Active Substance by Rhizophere Bacteria and their Effect on Plant Growth", 1970, 15(6), pp. 468–478 No Month.
Chemical Abstracts, vol. 81, No. 11, Sep. 16, 1974, p. 231, Ab.No.60637v.
Chemical Abstracts, vol. 89, No. 11, Sep. 11, 1978, p. 256, Ab.No.87260u.
Chemical Abstracts, vol. 77, No. 9, Aug. 28, 1972, p. 123, Ab.No.57484e.
John Davison, *Bio/Technology,* "Plant Beneficial Bacteria", vol. 6, Mar. 1988, pp. 282–286.
Harari, "The Involvement of Auxin in the Interaction Between Azospirillum spp. and Grass Roots"; (1985 Thesis, Hebrew University of Jerusalem) No. Month.
Kapulnik et al. "Changes in Root Morphology of Wheat Caused by Azospirillum Inoculation"; Can. J. Microbiol. 31: 881–887; No Date.
Kloepper & Schroth; "Plant Growth–Promoting Rhizobacteria and Plant Growth Under Gnotobiotic Conditions", Phytopathol. 71: 642–44 (1981). No. Month.
Van De Geijn et al.; "A Fast Screening Method for Bacterial Isolates Producing Substances Affecting Root–Growth" (presentation to 30th Meeting of the Societe Francaise de Phytopathologie, 14–17 Apr. 1986).
Hartmann et al.; "Isolation and Characterization of Azospirillum Mutants Excreting High Amounts of Indoleacetic Acid"; Can. J. Microbiol. 29: 916–923; No Date.

*Primary Examiner*—Ferris Lander
*Attorney, Agent, or Firm*—Fitzpatrick, Cella, Harper & Scinto

[57] ABSTRACT

Bacterial strains can be reproducibly isolated from soil that are root-colonizing and directly promote plant development. For example, strains of soil bacteria are provided that are good root colonizers and that promote plant growth under gnotobiotic conditions.

40 Claims, No Drawings

BACTERIAL CULTURES FOR ROOT-COLONIZING PLANTS

This application is a continuation of U.S. application Ser. No. 06/942,822 filed Dec. 17, 1986, now abandoned.

BACKGROUND OF THE INVENTION

Various strains of saprophytic soil bacteria are known to influence plant growth in different types of plants. For example, the inoculation of nonleguminous crops with selected strains of free-living, nitrogen-fixing species of Azotobacter and Azospirillum can cause significant increases in crop yield under field conditions. Kapulnik et al. (1981); Brown (1974). But bacteria of these genera are generally unable to compete adequately with native flora to assure multiplication. When used in seed inoculants, moreover, they are not "root colonizers," i.e., they are incapable of transferring in large numbers from seed to roots and, consequently, cannot keep pace with developing roots. See, e.g., Reynlers & Vlassak (1982). As a consequence, impractically large amounts of inoculum are required to obtain a meaningful effect on plant growth.

The mechanism(s) by which soil bacteria may influence plant growth has been the subject of extensive investigation. Research into the role of microbial iron transport agents (siderophores) in the root zones of plants (the "rhizosphere") indicates one mechanism by which some fluorescent pseudomonad species promote plant growth, namely, by antagonism (antibiosis, competition or exploitation) to deleterious indigenous microorganisms, resulting in their exclusion from roots. Kloepper et al (1980).

In this vein, it has been proposed that bacterial-mediated enhancement of plant growth generally involves interactions of the inoculated strain with rhizosphere microflora, possibly leading to the displacement of microorganisms detrimental to plant growth. For example, Canadian patent No. 1,172,585 discloses the use of particular strains of naturally-occurring pseudomonads to benefit plant growth in root crops by reducing the population of other indigenous root-zone microflora that adversely influence plant growth. Similarly, the results of one study indicated that growth-promotion in radish and potato by rhizobacteria did not occur under gnotobiotic conditions, when competition between other strains was not a factor, and hence, that rhizobacteria promote plant growth indirectly, by interaction of the rhizobacteria with native root microflora, rather than directly by microbial production of growth-promoting substances. Kloepper & Schroth (1981).

Another proposed mechanism for plant growth promotion by soil bacteria involves a direct stimulation of growth by bacterial elaboration of substances like nitrogen, plant hormones such as auxins and giberellins, and compounds that promote the mineralization of phosphates. But the hypothesis that elaboration of bacterial products is related to enhanced growth in plants has lacked definitive supporting data.

Thus, investigations of root-elongation promotion in grasses by an auxin-overproducer mutant of Azospirillum prompted the conclusion that observed levels of the bacterially-produced auxin bore no direct relation to the root elongation. A. Harari (1985). Using a petri plate bioassay for root elongation in wheat, Kapulnik et al (1985) found that seed inoculation with an A. brasilense strain resulted in root elongation in one bacterial concentration range but inhibition of root development in another, higher range. Kapulnik et al also reported that A. brasilense supernatants did not affect root length, a result militating against a substantial role for a bacterial product in promoting root elongation. A screening of rhizosphere bacterial metabolites for in situ effects on seedling root development likewise yielded mixed results, with the observed effects ranging from complete inhibition to unaffected development; notably, no growth stimulation per se was reported. Van De Geijn et al (1986).

Accordingly, there has been no clear indication heretofore that any soil bacteria might act directly to enhance root development, and certainly no showing of direct, bacterial-mediated stimulation of plant growth per se. Nevertheless, a bacterial strain capable of directly promoting plant growth, if one were isolated, could find immediate application, e.g., in soils where competition between introduced and native microflora did not result in a desired improvement in crop development. Such a direct-acting strain would be particularly useful under field conditions if it had the capacity to transfer from seed to developing roots, and to flourish in stable association with the root system of the maturing plant.

SUMMARY OF THE INVENTION

It is therefore an object of the present invention to provide, in a reproducible manner, strains of bacteria characterized by an ability to promote plant development directly, even under gnotobiotic conditions.

It is also an object of the present invention to provide a composition, comprising one or more such direct-acting bacterial strains, that can be employed in treating seeds or other plant material without the above-mentioned drawbacks associated with the use of known growth-promoting bacteria.

In accomplishing the foregoing objects, there has been provided, in accordance with one aspect of the present invention, a bacterial culture consisting essentially of at least one strain of bacteria that is root-colonizing and that directly promotes plant development. In accordance with another aspect of the present invention, a composition of matter has been provided that comprises an agriculturally-compatible carrier and at least one such strain of direct-acting, root-colonizing bacteria.

There has also been provided, in accordance with yet another aspect of the present invention, a method for promoting development of a plant, comprising the step of exposing seed from which the plant is grown to the aforesaid composition. In one preferred embodiment, the method of the present invention further comprises growing the seed under conditions such that competition between the bacterial strain in the composition and indigenous microbes plays substantially no role in the promotion of plant development by the bacterial strain.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

In this description, the term "root-colonizing" is used to denote bacteria, including rhizospheric and non-rhizospheric strains, that can transfer from seed (as an inoculum component) to roots developing from the seed, and are able to maintain a stable association with the root system of the plant as it grows. It has been discovered that a distinct subgroup of root-colonizing bacteria can be isolated from soil in a wide variety of habitats, the members of which subgroup possess the ability to cause significant, repeatable increases in the elongation and dry weight of shoots and roots, and in plant leaf area, under gnotobiotic conditions. Extensive selections from a large number of bacterial strains collected from the root zones of native plants growing in numerous locations in eastern Canada have shown that a small but reproducible percentage of the overall population of soil bacteria displays this trait. That these bacterial strains act directly to promote plant growth is further evidenced by the production of culture filtrates from the bacteria, as described below, that likewise stimulate plant growth.

The direct-acting, plant growth-promoting bacteria of the present invention can be identified from soil samples by the use of one or more gnotobiotic assays, as described in greater detail below. In a preliminary screening step, which is preferred, strains are isolated, e.g., following the procedures disclosed in copending U.S. application Ser. No. 898,042 (filed Aug. 19, 1986), the contents of which are hereby incorporated by reference; they are then identified, based on an observed ability to stimulate plant growth in raw field soil, as warranting further characterization.

The strains thus selected are thereafter screened for direct growth-promotion activity in a gnotobiotic assay. Those that test positive in such an assay can be used, in accordance with the present invention, to develop plant-treatment compositions, including seed inoculants, that contain whole bacterial cells or culture-filtrate material which acts directly to enhance plant growth. The soil bacteria isolated via gnotobiotic assay(s) can also be employed, pursuant to the present invention, to derive other direct-acting strains, for example, by mutagenesis, selective breeding or recombinant DNA techniques, which can be used in the same manner.

The gnotobiotic assays that are preferably employed to isolate bacterial strains within the present invention are described below:

Beaker Assay

A mixture of field soil and perlite is sterilized, e.g., by gamma-irradiation (about 1 mRad has proved suitable). Samples of the mix are transferred aseptically to sterile, covered beakers, to which enough water or nutrient solution is added to achieve a moisture content of roughly 25%. Surface-sterilized seed of a test plant, such as rape (*Brassica napus* and *Brassica campestris*), radish, wheat, soybean, corn or cotton, are then sown (1 seed per beaker) after briefly incubating in an aqueous bacterial cell suspension of the strain under study. (A bacterial concentration in the range of $10^9$ colony forming units (CFU) per ml of suspension has proved suitable for this purpose.) After seedlings have developed, under controlled conditions suitable to the test plant, to a point where mature leaves have grown, those plants subjected to bacterial treatments are compared against uninoculated controls to ascertain differences in leaf area between test and control groups.

Soil-plate assay

Petri plates are filled with ground, air-dried soil that has been sterilized by autoclaving, gamma-irradiation, etc. The soil in each plate is then moistened and left covered overnight to assure a uniform moisture distribution through the soil. Inoculated (test) and control seeds, as described above, are thereafter sown in each plate, some six to eight seeds per plate at about 1 cm depth, and grown in the dark under appropriate conditions of temperature and humidity until shoots develop. At the end of incubation, the shoot lengths are determined.

Growth pouch assay

Cellophane containers of the type heretofore used as seed-pack growth pouches are filled with a small volume of deionized water or mineral solution and autoclaved to assure sterility. Test seeds incubated in a bacterial suspension, as previously described, and control seeds not exposed to the bacteria are aseptically sown, about six seeds to a pouch, respectively, and are germinated in the dark under suitable, controlled conditions. After shoots have developed, the pouches are opened and the seedling root length, root dry weight, shoot length and shoot dry weight determined for both tests and controls.

The preceding assays can be used, either individually or in concert, to identify soil microorganisms displaying a property—the ability under gnotobiotic conditions to increase leaf area in 3- to 4-week old whole plants (beaker assay), to increase shoot length or shoot dry weight (soilplate assay), or to increase root length, root dry weight, shoot dry weight and shoot length (growth pouch assay)—that is positively correlated with the ability to promote growth directly in whole plants grown in raw (nonsterilized) soil. It has been found that bacterial strains which are characterized as direct growth-promoters by use of one or more of the assays detailed above are generally also root-colonizing, as defined previously, and are therefore particularly preferred components of seed inoculants. Root-colonizing capacity per se in a strain differentiated as direct-acting, pursuant to the present invention, can be assessed more precisely, if desired, following the technique of Scher et al (1984), the contents of which are hereby incorporated by reference.

By means of the above-described assays and a conventional serial-dilution technique, cultures of direct-acting bacterial strains within the present invention can be prepared in "biologically pure" form, i.e., in a culture where virtually all the bacterial cells present are of the selected strain. A biologically pure culture, thus defined, is a preferred embodiment of the present invention. Such a culture can be stored at −80° C. in glycerol, transferred to a bacteriological growing medium, incubated 1–2 days, centrifuged and mixed with water or buffer solution to create a suspension of bacterial cells for seed treatments. A biologically pure culture of the present invention can also be lyophilized and stored until a bacterial suspension of the selected strain is reconstituted by the addition of a suitable liquid carrier, such as oil, to the lyophilized culture. In any event, a culture of a direct-acting strain within the present invention can contain microorganisms that do not interfere with the growth-promoting action of the cultured strain.

For practical applications of strains of the present invention in agriculture, liquid bacterial suspensions of the sort described above are preferably employed. Thus, an agricultural composition comprising one or more bacterial strains that promote growth directly in plants are preferably dispersed in a liquid carrier, which is preferably an aqueous solution or water. For example, an aqueous solution of $MgSO_4$ (usually around 0.1M) can be used as a carrier to enhance bacterial viability over time. Alternatively, a buffer solution can be used as the liquid carrier. An aqueous bacterial suspension of the present invention can also contain alginate or a similar polysaccharide-containing material in sufficient amounts (typically about 1% by weight) to convert the aqueous suspension into a slurry. Optionally, an agriculturally-compatible oil (as defined below) can be added to the slurry to create an emulsion in which bacterial cells of the selected growth-promoting strain(s) are dispersed.

Bacteria-containing compositions within the present invention can also be based on an agriculturally-compatible oil medium in which a selected strain in dispersed. In this context, the phrase "agriculturally-compatible" denotes a substance that can be used routinely under field conditions without interfering with growers' planting equipment, and without adversely influencing crop development or the desired ecological balance in a cultivated area. Commercially available oils of this sort include mineral oil and vegetable oils, for example, soybean oil, canola (rapeseed) oil and corn oil. An oil-based carrier can be mixed with a xanthan gum or similar, agriculturally-compatible gum to produce a bacterial emulsion.

When a liquid carrier is employed according to the present invention, the resulting bacteria-containing composition can be mixed with seed or sprayed directly onto a field previously prepared for planting. Alternatively, a liquid bacterial suspension of the present invention can be absorbed into a granular carrier, such as pelleted peat or perlite granules, which is planted with the seed. Another alternative is to air-dry a liquid bacterial suspension of the present invention, at a temperature (typical range: 10°–30° C.) that is sufficiently low so as not to adversely affect viability of the bacterial cells, to form a powder. The bacteria-containing powder can then be mixed with oil or another suitable liquid carrier, or with a dry carrier like peat, talc or diatomaceous earth.

As indicated above, the direct-acting microorganisms of the present invention can be employed, in whole-cell form, in compositions further comprising an agriculturally-compatible carrier. A plant growth-promoting composition can also be prepared, in accordance with the present invention, using a filtrate material derived from a microorganism culture produced in the above-described manner. As described in greater detail below, a bacterial strain identified as direct-acting in accordance with the present invention is inoculated from an agar slant to a suitable nutrient medium and grown to late log phase. The resulting culture is used to inoculate a volume (typically, about 1 liter) of minimal medium (~pH 7.0; sterilized through 0.2μ filter). After some 72 hours of growth in culture the bacterial cells are harvested via centrifugation and the supernatant ("culture filtrate") is filter-sterilized to remove remaining cells. The culture filtrate is thereafter freeze-dried and reconstituted, in concentrate form, in deionized water. The culture filtrate can then be filter-sterilized and diluted to an appropriate concentration for testing via one or both of the growth pouch and soft agar assays, described above.

A culture filtrate thus prepared can also be further purified by separation into fractions, using conventional electrophoretic and/or chromatographic techniques. One such method, gel chromatography on Sephadex G-10, involves passing the liquid culture filtrate material through a vertical column containing a gel slurry (800–1000 mL volume), which separates the components of the filtrate according to their molecular weights (0–700 daltons on Sephadex G-10). The material eluting from the column is collected in fractions of 50–100 mL, is filter-sterilized, and is used as a seed treatment to test for root elongation in the gnotobiotic growth pouch assay.

The present invention is described in further detail by reference to the following illustrative examples. In the examples, strains selected as indicated were identified at least to genus by means of conventional indicators, including the following biochemical tests recommended by the American Society for Microbiology (ASM) in the MANUAL OF METHODS FOR GENERAL BACTERIOLOGY J24 (P. Gerhardt ed. 1981):

For confirmed Gram-negative strains—reaction profiles on API 20E test strips (product of Ayerst Labs, Inc., Plainview N.Y.); growth on MacConkey medium,; type of metabolism in OF glucose medium; production of DNAse; fluorescent pigment production; gelatin hydrolysis; nitrate reduction; starch hydrolysis; oxidase reaction; and lipase production (Tween 80 hydrolysis); urease production and motility.

For confirmed Gram-positive strains—growth on MacConkey medium; type of metabolism in OF glucose medium; catalase test; gelatin hydrolysis; Voges-Proskauer reaction; indole production; citrate utilization; motility; urease production; endospore formation; and acid production from glucose, saccharose or mannitol. Example 1

Promotion of Plant Growth in a Gnotobiotic Soil System

Samples (110–120 grams) of a field soil: perlite mix previously sterilized by gamma-irradiation (1 mRad) were each transferred to covered beakers, as described above, for use in a beaker-assay screening of thirty bacterial strains which had been isolated from soil around indigenous grasses growing in the Canadian High Arctic. (The thirty strains had been selected for screening based on the observed ability of each to promote growth, as gauged by increased leaf area and root dry weight, of canola plants grown from inoculated seed in raw soil.) More specifically, groups of surface-sterilized canola seeds were each incubated briefly in an aqueous suspension ($10^9$ CFU/ml) of a selected strain before being sown, one seed per beaker, in a moisture-equilibrated, sterile soil sample.

After three to four weeks under controlled conditions (temperature: 13°–14° C.; 12 hours light), seedlings grown from bacterially-treated seeds were harvested and compared to uninoculated controls for differences in leaf area. Each of the thirty strains tested were found to have established populations, in the range of LOG 5–7 per gram, in the gnotobiotic assay system. But only certain strains, particularly the initial seven strains listed in Table 1 below, demonstrated consistent growth-promoting activity in the sterile system. Conversely, several of the assayed strains routinely exhibited detrimental effects on seedling development in sterilized soil, despite having stimulated growth in plants grown in raw soil.

TABLE 1

EFFECT OF BACTERIAL TREATMENT ON CANOLA GROWTH IN A GNOTOBIOTIC SOIL ASSAY

| STRAINS | MEAN % CHANGE IN LEAF AREA FROM UNTREATED CONTROLS |
|---|---|
| Pseudomonas putida 25-71 | +24 |
| Serratia liquefaciens 1-141 | +44 |
| Pseudomonas sp. 37-8 | +20 |
| P. fluorescens X. | +18 |
| P. fluorescens 54-4 | +10 |
| P. putida biovar B 25-33 | +17 |
| S. liquefaciens 2-16 | +22 |
| P. putida 54-26 | +18 |
| P. fluorescens G3-8 | +13 |
| P. fluorescens 36-44 | +17 |
| P. fluorescens 31-44 | +10 |

TABLE 1-continued

EFFECT OF BACTERIAL TREATMENT ON CANOLA GROWTH IN A GNOTOBIOTIC SOIL ASSAY

| STRAINS | MEAN % CHANGE IN LEAF AREA FROM UNTREATED CONTROLS |
|---|---|
| P. fluorescens 39-8 | +9 |
| P. putida G3-9 | +3 |
| P. fluorescens 63-49 | +3 |
| Arthrobacter citreus 44-9 | 0 |
| P. fluorescens 36-43 | 0 |
| P. fluorescens 37-9 | −8 |
| P. fluorescens 63-14 | −9 |
| P. putida 56-13 | −11 |
| Pseudomonas sp. 62-34 | −12 |
| P. fluorescens 61-16 | −13 |
| P. fluorescens 46-8 | −13 |
| P. putida 17-114 | −18 |
| P. fluorescens 63-28 | −14 |
| P. fluorescens 34-13 | −15 |
| P. fluorescens 31-12 | −13 |
| P. fluorescens 34-36 | −18 |
| P. fluorescens G8-17 | −21 |
| P. fluorescens 62-24 | −24 |
| P. putida 63-36 | −25 |

The growth-promoting activity of those strains testing positive in the beaker assay was unaffected by an increasing of the bacterial cell density in the seed inoculum. This observation, coupled with the fact that all the tested strains were root-colonizing, militates against a direct causal connection between root-colonizing ability in the assay plant and growth promotion under gnotobiotic conditions by a given microbe. The gnotobiotic growth-stimulating activity was also detected in assay systems where no nutrients were added to the sterilized soil, i.e., the positive effects of the inoculated bacteria were not strictly nutrient-dependent.

Example 2

Growth-Promoting Activity of Bacterial Culture Filtrates

Thirteen strains that were active in a gnotobiotic soil system as described above were further screened, via two or three repetitions of a soil-free, soft agar assay, for activity indicative of direct promotion of plant growth. In the soft agar assay, biologically pure "starter" cultures of the strains listed in Table 2 below were inoculated into Tryptic Soy Broth (Difco) or Nutrient Broth, and were grown with agitation (100 rpm at 30° C.) to a late log phase over about 15 hours. Each starter culture in complex medium was used as an inoculum for a corresponding "working" culture grown for 72 hours (100 rpm at 30° C.) on minimal medium [0.01M potassium phosphate, 0.5 g/l magnesium sulfate, 1.0 g/l ammonium chloride, 10 g/l glucose (pH 7.0)] or on 5% canola seed exudate pursuant to Scher et al (1985).

After incubation, each working culture was centrifuged to remove bacterial cells, and the supernatant fraction filtered (0.2μ) to free the filtrate of remaining bacteria. The filtrate was freeze-dried and then reconstituted in water to about five times the original concentration. The concentrated filtrate was filter sterilized (0.2μ), after which it could be stored in a freezer without loss of activity.

Canola seeds were surface-sterilized prior to treatment with the bacterial culture filtrates and, thereafter, were planted in sterile, agar-containing tubes. Two methods were used to treat the seed: (a) soaking in the filtrate before planting; and (b) application of the filtrate by inoculation (25μ) after planting of the seed. Following the treatment, the seeds were sown on the surface of 12 ml of 0.3% agar (w/v) in 15×150 mm glass tubes (1 seed/tube; 36 tubes/treatment).

After seven days incubation, the seedlings were removed from the tubes and the root lengths measured for differences relative to control treatments (water or uninoculated medium). As shown in Table 2, culture filtrates derived from ten of the thirteen assayed strains consistently caused a statistically significant increase in root length over that of the controls.

TABLE 2

EFFECT OF INOCULATION OF CANOLA SEEDS WITH CULTURE FILTRATES ON ROOT ELONGATION IN SOFT AGAR TUBES

| Treatment (Strain Filtrate) | Response Over Multiple Trials |
|---|---|
| Arthrobacter citreus 44-9 | +3/3 |
| Pseudomonas fluorescens 63-49 | +3/3 |
| Pseudomonas fluorescens 36-43 | +2/2 |
| Pseudomonas fluorescens 31-12 | +2/2 |
| Pseudomonas fluorescens X | +2/2 |
| Pseudomonas putida 25-71 | +2/2 |
| Serratia liquefaciens 2-16 | +2/3 |
| Pseudomonas fluorescens 62-24 | +1/2 |
| Serratia liquefaciens 2-20 | −2/2 |
| Pseudomonas putida 17-114 | −2/2 |
| Serratia liquefaciens 1-141 | −3/3 |

Filtrates of strains cultured in seed exudate broth promoted root elongation to a somewhat lesser extent than when cultured in minimal medium, raising the possibility that the observed root-elongating activity was substrate dependent. However, filtrates obtained from cultures grown with different sugars and amino acids as carbon sources, respectively, did not differ in activity. Moreover, the inactivity of both the uninoculated medium and the seed exudate broth in promoting root elongation argues against simple nutritional stimulation of root growth.

When a culture filtrate of the direct-acting strain Pseudomonas putida GR12-2 (see Example 3 below) was separated into fractions over a Sephadex G-10 gel column, as previously described, the eluted fractions were tested, by means of the gnotobiotic growth pouch assay, as seed inocula on canola seed. The results of the assay, summarized in Table 3, evidence the presence of relatively small, plant-growth-regulating molecules in the different molecular-weight fractions eluted from the column. The existence of such growth regulators in the culture filtrates of direct-acting bacteria within the present invention is further indicated by test data, enumerated in Table 4, that show a concentration-dependent variation in the root-elongating activity of GR12-2 culture filtrate in the gnotobiotic growth pouch assay.

TABLE 3

EFFECT OF GR12-2 CULTURE-FILTRATE GEL CHROMATOGRAPHIC FRACTIONS ON CANOLA ROOT ELONGATION IN STERILE GROWTH POUCHES

| Fraction[a] | X̄ % Increase in Root Length Over Untreated Controls[b] |
|---|---|
| CF[c] | 23 |
| Fraction 1 | 12 |
| 2 | 20 |
| 3 | 15 |
| 4 | 29 |
| 5 | 16 |
| 6 | 10 |
| 7 | 6 |

TABLE 3-continued

EFFECT OF GR12-2 CULTURE-FILTRATE GEL
CHROMATOGRAPHIC FRACTIONS ON CANOLA ROOT
ELONGATION IN STERILE GROWTH POUCHES

| Fraction[a] | X̄ % Increase in Root Length Over Untreated Controls[b] |
|---|---|

[a]Twenty-fold concentrated culture filtrate from a 72-hour GR12-2 culture separated on Sephadex G-10. Eluted fractions were tested as seed inoculum on canola in growth pouches.
[b]Values represent results from bioassays conducted on fractions collected in eight independent separations.
[c]CF: non-fractionated culture filtrate at 10-fold concentration, relative to the original culture.

TABLE 4

EFFECT OF CONCENTRATION OF GR12-2 CULTURE
FILTRATE ON CANOLA ROOT ELONGATION IN
STERILE GROWTH POUCH ASSAYS

| Concentration Of Culture Filtrate[a] | X̄ Root Length[b] (mm) | % Change Over Untreated Controls[c] |
|---|---|---|
| 1/10 | 55.9 | 25 |
| 1 | 63.6 | 42 |
| 10 | 72.4 | 62 |
| Control | 44.8 | — |

[a]Filtrates obtained from 72-hour bacterial cultures were concentrated to dryness, resuspended in deionized water to a 10-fold concentration, 10-fold relative to the original culture suspension, and then sterilized and diluted for testing.
[b]Values represent means from two independent experiments, each using ten replicate growth pouches, each sown with six seeds, per treatment.
[c]Control treatments were seeds incubated in sterile deionized water.

Example 3

Further Characterization of a Bacterial Strain that Directly Promotes Plant Growth An arctic-diazotrophic, nitrogen-fixing pseudomonad, *P. putida* GR12-2, was selected from the rhizosphere of an eastern Canadian habitat, based on the ability of the strain to stimulate the growth of canola plants in raw soil. Additional characteristics of GR12-2 are enumerated in Table 5. A culture of GR12-2 is deposited at the American Type Culture Collection (Rockville, Md.) under accession No. 53,555.

TABLE 5

CHARACTERISTICS OF *PSEUDOMONAS PUTIDA* GR12-2

| Character | Reaction* |
|---|---|
| Colony morphology | Smooth, entire, with fluorescent-green pigment on PAF |
| Cells morphology | Rod, one end pointed |
| Flagella | 1–2 |
| Gram stain | − |
| Growth in pH 6 | + |
| Growth in pH 8 | + |
| Growth at 4° C. | + |
| Growth at 30° C. | + |
| Growth at 37° C. | − |
| Growth in 3% NaCl | − |
| Doubling time at 25° C. | 90 minutes |
| Nitrogenase at 4° C. | + |
| Nitrogenase at 25° C. | + |
| Nitrogenase at 30° C. | − |
| Growth in MacConkey agar | + |
| Growth in skim milk | + |
| Growth on acetate as SCS | + |

TABLE 5-continued

CHARACTERISTICS OF *PSEUDOMONAS PUTIDA* GR12-2

| Phenylalanine deamination | − |
|---|---|
| Nitrate to nitrite | − |
| Nitrite reduction | − |
| Nitrite to $N_2$ | − |
| Arginine (Mollers) | + |
| Gelatinase | − |
| Urease | − |
| Cytodirone oxidase | + |
| Lysine decarboxylase | − |
| Ornithine decarboxylase | − |
| Lecithinase | − |
| Phosphatase | + |
| Catalase | + |
| Oxidase | + |
| Melobiose | + |
| β-glucosidase | − |
| Deoxyribonuclease | − |
| Tryptophane deaminase | − |
| Mannitol acidification | + |
| Sorbitol acidification | − |
| Inositol acidification | − |
| D-mannose | + |
| L-rhamnose | − |
| D-ribose | + |
| Growth on Simmons citrate | + |
| Growth on dl-hydroxybutyrate | + |
| Growth on 0.05% centrimide | + |
| Growth on Antibiotic: | |
| Kanamycin (10 ppm) | − |
| Chloramphenicol (10 ppm) | − |
| Tetracycline (10 ppm) | − |
| Fluorescein production | + |
| Other pigments | − |
| $H_2S$ production | − |
| Indole production | − |
| Pyocyanin production | − |
| Pyoverdin production | + |
| 3-Ketolactose from lactose | − |
| Casein hydrolysis | − |
| Starch hydrolysis | − |
| Tween 20 hydrolysis | + |
| Tween 80 hydrolysis | + |
| Testosterane degradation | − |
| Tyrosine degradation | + |
| Fermentation with D-glucose | − |

| Character | Reaction** |
|---|---|
| Formation of acid from: | |
| L-arabinose | + |
| Cellobiose | K |
| Ethanol | + |
| D-fructose | + |
| D-glucose $AO_2$ | + |
| D-glucose $AnO_2$ | − |
| Glycerol | + |
| i-inositol | K |
| D-mannitol | + |
| D-mannose | + |
| L-rhamnose | + |
| D-ribose | + |
| Lactose | K |
| Maltose | K |
| Sucrose | K |
| Trehalose | K |
| D-xylose | + |
| Control | K |

*Reactions:
+, growth and (or) activity;
−, no growth and (or) no activity.
**K: alkaline
+: acid
−: no change GR12-2 was subjected to the soil-plate assay described previously, with autoclaved clay loam (pH 7.0), moistened with sterile solution of 1 mM $K_2HPO_4$ or deionized water only, used as the sterile soil for inoculated and control canola seeds. After the seeds were sown, the plates were incubated in the dark for five days at 20° C. and 100% real humidity. The effect bacterial inoculation had in promoting growth in canola is evident from the test results set out in Table 6:

TABLE 6

THE EFFECT OF ADDED $K_2HPO_4$ AND BACTERIAL INOCULATION ON CANOLA SHOOT LENGTH IN THE SOIL-PLATE ASSAY

| Soil Moisture (% v/w) | Added $K_2HPO_4$ (mM/g air-dried soil) | Bacterial Inoculation | Shoot Length (mm) |
|---|---|---|---|
| 15 | 0 | + | 31.0 |
| 15 | 0 | – | 21.0 |
| 15 | 15 | + | 31.1 |
| 15 | 0 | – | 32.7 |
| 20 | 0 | + | 49.7 |
| 20 | 0 | – | 31.9 |
| 20 | 20 | + | 47.5 |
| 20 | 20 | – | 38.3 |
| 25 | 0 | + | 47.1 |
| 25 | 0 | – | 35.4 |
| 25 | 25 | + | 45.3 |
| 25 | 25 | – | 41.2 |
| LSD p = 0.05 | | | 9.8 |
| LSD p = 0.01 | | | 12.5 |

When no phosphate was added to the plates, shoot elongation was enhanced by 47.6, 40.4 and 33.1% at 15, 20 and 25% moisture, respectively. These effects were all significant at R=0.05 (see Table 4). The addition of phosphate ($K_2HPO_4$) to uninoculated seeds increased shoot elongation significantly (R=0.05) at 15% moisture. With higher moisture levels or with inoculated seedlings, however, the effect of the phosphate was not significant at p=0.05.

Three GR12-2 mutants that are nitrogen-fixation deficient (nif–) were prepared by transposon mutagenesis. More specifically, transposon Tn5 was introduced into cells of the parent strain via conjugation on membrane filters. *E. coli* cells containing a "suicidal vehicle" pHKK 23::Tn5 were used as donors in intergeneric matings with rifampicin-resistant GR12-2 recipients. Donors and recipient bacteria (LOG 8 of each) were mixed and filtered through a sterile, cellulose nitrate Millipore filter (0.45 µm porosity, 45 mm diameter). The filter bearing donors and recipients was placed on the surface of Pseudomonas agar F (PAF, a product of Difco) and incubated for 12–15 hours at 25° C. After this time, the cells were washed off the filter, resuspended in Tryptic Soy Broth and plated on the selective media. The transconjugants were selected on PAF supplemented with rifampicin (100 µg/ml). Transconjugant colonies were purified and used to test for negative acetylene reduction activity (ARA), an indicator of nitrogen fixing ability, according to the procedure of Lifshitz et al (1986).

The GR12-2 parent strain and three derivative nif– mutants, designated "GR12-2/16," "GR12-2/25" and "GR12-2/764," respectively, were each screened via the growth pouch assay described above. More specifically, seed-pack growth pouches (Northrup King Co., Minn. 33440) were filled with 10 ml deionized water or mineral solution (either 1 mM $KH_2PO_4$ or 100 µg/ml $NH_4NO_3$) and autoclaved for 60 minutes at 121° C. Canola seeds were surface sterilized by soaking in 1% sodium hypochlorite solution for 10 minutes, followed by thorough rinsing in sterile water and air-drying overnight in a flow-hood.

Bacterial cultures (20 ml) were grown in Tryptic Soy Broth in 250 ml flasks shaken at 100 rpm and at 25° C. for 20 hours. Bacterial cells were then washed (twice) in 0.1M $MgSO_4$ buffer, and the optical density of the suspension was adjusted to contain LOG 7.8 CFU/ml (unless otherwise indicated below). Surface sterilized seeds were soaked in bacterial suspensions for 60 minutes, then aseptically sown in the growth pouches (6 seeds/pouch). The pouches were incubated in the dark at 20° C. for six days. At the end of incubation the pouches were opened and the seedling root length was determined.

The bacterial density on the seeds (after soaking) or on the roots (at the end of the incubation period) was determined by washing in 9 ml of sterile buffer (0.1M $MgSO_4$) with a vortex blender for 15 seconds. The bacterial suspension was plated on PAF, using a spiral plater (Spiral System Inc., Bethesda Md. 20814). After 48 hours of incubation at 25° C., colonies were counted using a laser counter (Model 500A, Spiral Systems).

The canola seedlings treated with *P. putida* GR12-2 developed significantly longer roots than untreated (nonbacterized) seedlings in growth pouches (Table 7). Seed treatment with autoclaved (dead) bacteria or bacteria treated with kanamycin (inhibitory to GR12-2) had no effect on root elongation. The three nif– mutants strain GR12-2 also significantly enhanced root elongation (p=0.01), similarly to the wild-type strain (Table 8).

TABLE 7

THE EFFECT OF *P. PUTIDA* GR12-2 ON CANOLA ROOT ELONGATION IN GROWTH POUCHES

| Seed Treatment[a] | Root Length (mm)[b] |
|---|---|
| GR12-2 | 59.2**[c] |
| GR12-2 autoclaved | 37.1 |
| GR12-2 + kanamycin[d] | 35.5 |
| Kanamycin control | 34.6 |
| Buffer control | 31.4 |

[a]Seeds were soaked in a bacterial suspension (LOG 7.8 CFU/ml 0.1M $MgSO_4$) for 60 minutes which gave LOG 4.9 CFU/seed, prior to sowing in the growth pouch.
[b]The root length was determined after 6 days of incubation at 20° C. in the dark.
[c]**Significantly different from the buffer control treatment at p = 0.01, according to a Fisher least-significant difference (FLSD) analysis of variance.
[d]Kanamycin was suspended in 0.1M $MgSO_4$, 100 µg/ml, then filter-sterilized through 0.2 µmembrane. Bacteria were suspended in kanamycin solution (LOG 7.8 CFU/ml), prior to the seed treatment.

TABLE 8

COMPARATIVE EFFECT OF *P. PUTIDA* GR12-2 AND DERIVATIVE nif– MUTANTS ON CANOLA ROOT ELONGATION IN GROWTH POUCHES

| Strain[a] | Root Length (mm)[b] |
|---|---|
| GR12-2 | 60.5**[c] |
| GR12-2/16 | 59.0** |
| GR12-2/25 | 57.51** |
| GR12-2/764 | 56.9** |
| Control | 37.3 |

[a]Seeds were soaked in a bacterial suspension (LOG 7.8 CFU/ml in 0.1M $MgSO_4$) for 60 minutes which gave LOG 4.9 CFU/seed prior to sowing in the growth pouch.
[b]The root length was determined after 6 days of incubation at 20° C. in the dark.
[c]**, *Significantly different from the buffer control treatment at p = 0.01 and p = 0.05, respectively, according to a FLSD analysis of variance.

As the data in Table 9 demonstrate, increasing amounts of ammonium nitrate in the growth-pouch system had the same qualitative effect on canola seedling root length in inoculated and non-bacterized plants. The root length of control seedlings was reduced by 22% (p=0.01) when grown in 100 µg $NH_4NO_3$/ml as compared to their growth in water only (see Table 9). Further increases in the amount of ammonium nitrate in the growth solution, up to 1000 µg $NH_4NO_3$/ml, consistently decreased the mean root length as much as 33.9%, as compared to the water control. Bacterized seedlings grown at 100 µg $NH_4NO_3$/ml had 19.8% shorter roots than bacterized seedlings grown in water (p=0.01). At a level of 1000 µg $NH_4NO_3$/ml, the mean root length of bacterized seedlings was 54.6% less than bacterized seedlings grown in water.

TABLE 9

THE EFFECT OF THE EXTERNAL CONCENTRATION OF $NH_4NO_3$ AND BACTERIAL INOCULATION IN GROWTH POUCHES ON CANOLA ROOT LENGTH

| $NH_4NO_3$ (mM)[a] | Bacterial Inoculation[b] | Root Length[c] (mm) |
|---|---|---|
| 0 | + | 70.0 |
| 0 | − | 42.8 |
| 0.13 | + | 73.5 |
| 0.13 | − | 47.2 |
| 0.31 | + | 75.5 |
| 0.31 | − | 48.2 |
| 0.63 | + | 64.1 |
| 0.63 | − | 45.2 |
| 1.25 | + | 56.2 |
| 1.25 | − | 33.5 |
| 2.50 | + | 44.1 |
| 2.50 | − | 37.6 |
| 6.25 | + | 41.6 |
| 6.25 | − | 30.0 |
| 12.5 | + | 31.8 |
| 12.5 | − | 28.3 |
| LSD $p$ = 0.05 | + | 7.7 |
| LSD $p$ = 0.01 | − | 10.2 |

[a]The growth pouch contained 10 ml of $NH_4NO_3$ at various concentrations.
[b]Seed of Brassica campestris cv. "Tobin" were soaked in bacterial suspension (P. putida GR12-2, LOG 7.8 CFU/ml in 0.1M $MgSO_4$) for 60 minutes, which gave LOG 4.9 CFU/seed prior to sowing in the growth pouches.
[c]The root length was determined after 6 days of incubation at 20° C. in the dark.

These data on promotion of plant growth by the GR12-2 strain do not support a causal link to bacterial nitrogen fixation because (i) the addition of mineral nitrogen (ammonium nitrate) decreased, rather than increased, root elongation and (ii) nif[−] mutants of the strain retained the ability to enhance root elongation. In addition, other wild-type pseudomonads isolated in accordance with the present invention that did not fix nitrogen were nevertheless found to be active in enhancing root elongation.

It was also determined that canola seedlings inoculated with P. putida GR12-2 developed longer roots than uninoculated seedlings in growth pouches supplemented with water only or water with 1 mM potassium phosphate-buffer at pH levels between 5 to 8 (see Table 10). The root lengths of both inoculated and uninoculated seedlings were also increased in the phosphate buffer solution as compared to the root lengths of seedlings grown in water only.

TABLE 10

THE EFFECT OF POTASSIUM PHOSPHATE-BUFFER (pH) AND BACTERIAL INOCULATION ON CANOLA ROOT LENGTH IN GROWTH POUCHES

| Buffer pH[a] | Bacterial Inoculation[b] | Root Length[c] (mm) |
|---|---|---|
| 5 | + | 63.7 |
| 5 | − | 40.3 |
| 6 | + | 54.5 |
| 6 | − | 40.7 |
| 7 | + | 62.8 |
| 7 | − | 45.4 |
| 8 | + | 57.3 |
| 8 | − | 43.8 |
| $H_2O$ control | + | 49.4 |
| $H_2O$ control | − | 30.0 |
| LSD $p$ = 0.05 | | 10.2 |
| LSD $p$ = 0.05 | | 13.5 |

[a]The growth pouch contained 10 ml of 1 mM potassium phosphate-buffer of adjusted pH.
[b]Seeds of Brassica campestris cv. "Tobin" were soaked in bacterial suspension (LOG 7.8 CFU/ml in 0.1M $MgSO_4$) for 60 minutes, which gave LOG 4.9 CFU/seed prior to sowing in the growth pouch.
[c]The root length was determined after 6 days of incubation at 20° C. in the dark.

TABLE 11

THE EFFECT OF THE EXTERNAL CONCENTRATION OF $K_2HPO_4$ AND BACTERIAL INOCULATION ON CANOLA ROOT LENGTH, SHOOT LENGTH, ROOT DRY WEIGHT AND SHOOT DRY WEIGHT IN GROWTH POUCHES

| $K_2HPO_4$[a] (mM) | Bacterial Inoculation[b] | Root Length[c] (mm) | Shoot Length (mm) | Root Dry Weight (mg) | Shoot Dry Weight (mg) |
|---|---|---|---|---|---|
| 0 | + | 70.4 | 36.4 | 0.272 | 1.667 |
| 0 | − | 48.0 | 28.8 | 0.254 | 1.313 |
| 0.01 | + | 75.6 | 35.8 | 0.260 | 1.626 |
| 0.01 | − | 46.4 | 29.1 | 0.253 | 1.469 |
| 0.05 | + | 79.3 | 44.8 | 0.295 | 1.781 |
| 0.05 | − | 49.8 | 31.8 | 0.274 | 1.519 |
| 0.1 | + | 80.7 | 45.9 | 0.321 | 1.981 |
| 0.1 | − | 55.2 | 33.6 | 0.267 | 1.791 |
| 0.5 | + | 86.8 | 49.3 | 0.314 | 2.016 |
| 0.5 | − | 58.4 | 33.5 | 0.293 | 1.772 |
| 1 | + | 86.0 | 44.9 | 0.291 | 1.981 |
| 1 | − | 60.3 | 36.8 | 0.256 | 1.891 |
| 10 | + | 72.4 | 46.2 | 0.263 | 2.033 |
| 10 | − | 35.8 | 35.8 | 0.226 | 2.000 |
| LSD $p$ = 0.05 | | 8.8 | 3.5 | 0.063 | 0.379 |
| LSD $p$ = 0.01 | | 11.6 | 4.6 | 0.084 | 0.500 |

[a]The growth pouch contained 10 ml of $K_2HPO_4$ at different concentrations.
[b]Seed of Brassica campestris cv. "Tobin" were soaked in bacterial suspension (LOG 7.8 CFU/ml in 0.1M $MgSO_4$) for 60 minutes, which gave LOG 4.9 CFU/seed prior to sowing in the growth pouch.
[c]The root and shoot length and dry weight were determined after 6 days of incubation at 20° C. in the dark.

The combined effects of $K_2HPO_4$ and P. putida GR12-2 were found to be additive (see Table 11); hence, root and shoot lengths were greater for plants receiving combined treatments of $K_2HPO_4$ and bacteria than for plants receiving single treatments of either bacteria or $K_2HPO_4$ alone.

To determine if the effect of potassium phosphate-buffer on root elongation was due to the supply of potassium or due to the supply of phosphate, solutions of the following minerals were assayed in the growth pouch system at concentrations of 1 mM: $Na_2HPO_4$, $NaH_2PO_4$, $KH_2PO_4$, KCl, $K_2SO_4$, NaCl, $Na_2SO_4$. All the solutions containing phosphate ($K_2HPO_4$, $Na_2HPO_4$, $NaH_2PO_4$) increased root elongation significantly (p=0.05) over water control, by 19.0, 17.1, 15.9 and 12.9%, respectively. On the other hand, no effect was detected with solutions of KCl, $K_2SO_4$, NaCl and $Na_2SO_4$.

The combined effects of bacterial inoculation and the concentration of $K_2HPO_4$ on canola seedling growth was determined for root length, shoot length, root dry weight and shoot dry weight (see Table 8 above). Generally, the bacteria treatment increased seedling development with regard to all of these criteria. The amount of phosphate in the growth solution clearly affected seedling growth in growth pouches. Root length and dry weight of either inoculated or uninoculated seedlings was best when $K_2HPO_4$ was supplied at concentrations between 0.1 to 1 mM. The shoot length of inoculated seedlings significantly increased (p=0.01) when $K_2HPO_4$ was supplied at concentrations equal or greater than 0.05 mM. Shoot dry weight of both inoculated and uninoculated seedlings was generally consistent with increasing the concentrations of $K_2HPO_4$ in the growth solution. Moreover, linear regression analysis indicated significant correlations (p=0.01) between root length and root weight ($R^2$=0.26100), between root length and shoot length ($R^2$=0.48711), and between root length and shoot weight ($R^2$=0.19087) in inoculated seedlings.

A direct effect on phosphate uptake by canola seedlings treated with growth-promoting bacteria of the present invention was determined by including $^{32}$p-labelled phosphate in the growth pouch solution. Potassium phosphate (1 mM) in deionized water was labelled with $^{32}PO_4$ (New England Nuclear) at a final concentration of 5 μCi per ml. At the end of incubation (21 days at 12° C., shoots and roots were separated and washed three times in 1 mM $K_2HPO_4$ to remove the superficial radioactivity. The amount of radioactive phosphorus in roots and shoots was assayed using a gamma scintillation counter.

The results (Table 12) show clear increases in the levels of $^{32}$p in inoculated roots (100.4% over uninoculated seedlings; significant at p=0.05) and in the levels of $^{32}$p in inoculated shoots (123.4% increase over uninoculated seedlings; significant at p=0.01). Linear regression analysis indicated significant correlations (p=0.01) between root length and the level of $^{32}$p in roots ($R^2$=0.2226) and between root length and the level of $^{32}$p in shoots ($R^2$=0.3638). Thus, the increased root elongation observed under gnotobiotic conditions with the addition of phosphate ions ($H_2PO$, $HPO_4^{-2}$) to the growth solution was also correlated with a markedly increased uptake of labelled phosphorus by the roots and translocation of that phosphorus into the shoots. Moreover, the data show a simultaneous enhancement of root growth and shoot development (i.e., an overall stimulation of growth as opposed to a specific target effect) by direct-acting bacteria of the present invention, a phenomenon not heretofore associated with the action of any phytohormone.

TABLE 12

THE EFFECT OF THE BACTERIAL INOCULATION ON ROOT-LENGTH, SHOOT-LENGTH, $^{32}$P UPTAKE BY ROOT AND BY SHOOT, RESPECTIVELY, OF CANOLA SEEDLINGS GROWN IN GROWTH POUCHES

| Bacterial Inoculation[a] | Root Length[b] (mm) | Shoot Length (mm) | $^{32}$P in Root (cpm)[c] | $^{32}$P in Shoot (cpm) |
|---|---|---|---|---|
| + | 64.3 | 31.6 | 980.4 | 648.2 |
| − | 53.4 | 24.5 | 489.2 | 290.2 |
| LSD p = 0.05 | 9.7 | 5.9 | 455.7 | 234.1 |
| LSD p = 0.01 | NS[d] | NS | NS | 314.7 |

[a] Seeds of *Brassica campestris* cv. "Tobin" were soaked in bacterial suspension (LOG 7.8 CFU/ml in 0.1M $MgSO_4$) for 60 minutes, which gave LOG 4.9 CFU/seed prior to sowing in the growth pouch.
[b] Root length, shoot length, $^{32}$P in root and $^{32}$P in shoot was determined after 21 days of incubation at 12° C. in the dark.
[c] The growth pouch contained 10 ml of 1 mM $K_2HPO_4$ labelled with $^{32}$P at 5 μCi/ml.
[d] NS: "Not significant".

EXAMPLE 4

Correlation Between Bacterial Activity in a Gnotobiotic Assay and Enhanced Growth in Raw Soil Several soil bacteria strains identified as being gnotobiotically active, in accordance with the present invention, were each tested for the ability to promote the growth of plants grown in raw soil under greenhouse conditions. More specifically, the test bacteria were grown for 24 hours in Tryptic Soy Broth, centrifuged and adjusted, by use of 0.1 M magnesium sulphate solution, to an optical density of 0.05 at an absorbance of 780 nm, corresponding to Log 7.7 CFU/ml. Pots of 6 cm in diameter were filled with soil mix (40% field soil, 40% perlite and 20% coarse sand) and watered, and three holes, each 1 cm deep, were made per pot. One canola seed was planted in each hole, and 1 ml of bacterial suspension applied per pot. Each treatment was replicated 8 to 10 times in a random block design. Controls consisted of seeds planted in the same manner with magnesium sulphate solution substituted for the bacterial suspension.

Pots were placed in a phytotron at a day temperature of 20° C. and a night temperature of 18° C. After emergence, the plants were thinned to one per pot. Seventeen to eighteen days after planting, the plants were harvested, and the leaf area and dry weight of each plant was recorded; data were analyzed for significance by means of a 2-way analysis of variance.

As shown in Table 13, the incidence of bacterial activity in any one of the gnotobiotic assays described above correlated well with significant growth promotion in the greenhouse assay.

TABLE 13

COMPARISON OF DIFFERENT BIOASSAYS WITH REGARD TO BACTERIAL ACTIVITY ON CANOLA

| Strain | Greenhouse Assays | Gnotobiotic Soil Assays | Root Elongation in Growth Pouches | Root Elongation in Agar Tubes |
|---|---|---|---|---|
| *P. putida* 25-71 | + | + | + | + |
| *P. putida* 25-33 | + | + | + | + |

TABLE 13-continued

COMPARISON OF DIFFERENT BIOASSAYS WITH
REGARD TO BACTERIAL ACTIVITY ON CANOLA

| Strain | Green-house Assays | Gnoto-biotic Soil Assays | Root Elongation in Growth Pouches | Root Elongation in Agar Tubes |
|---|---|---|---|---|
| S. liquefaciens 2-16 | + | + | NT* | + |
| P. fluorescens X | + | + | + | + |
| S. liquefaciens 1-141 | + | + | NT* | + |

*"Not Tested"

Tests were also conducted to show the ability of direct-acting bacterial strains within the present invention to increase yield in an important agronomic crop (canola) under field conditions. In the tests, four trials were conducted with *Brassica napus* cv. "Westar" and four others with *Brassica campestris* cv. "Tobin." All trials were of the randomized block design, with six to eight replications; each replication involved a plot of four to six, 6-meter-long rows. Planting and harvesting was accomplished mechanically. Yield was determined by taking seed weight per plot (at full maturity) and adjusting to 10% seed moisture.

The results (see Table 14) demonstrated a good correlation between yield-enhancement by a given strain and the activity of that strain in a gnotobiotic assay. Where such correlation was lacking, as for *P. putida* GR19-1, the disparity in results under sterile-assay and field conditions may be attributed to a sensitivity of the tested strain to differences in climatic factors between its native habitat and the trial location.

TABLE 14

EFFECT OF DIRECT-ACTING BACTERIAL STRAINS
ON CANOLA
ROOT ELONGATION IN GROWTH POUCHES AND ON
CANOLA YIELD IN FIELD TRIALS

| Strain | % Increase In Root Length Over Control In Sterile Growth Pouches | % Increase In Canola Yield Over Carrier Control Across 8 Field Trials |
|---|---|---|
| P. Putida GR12-2 | 79.9 | 6.3 |
| P. fluorescens X | 55.0 | 8.4 |
| Pseudomonas sp. G1-1 | 35.0 | 4.2 |
| P. putida biovar B 25-33 | 27.3 | 3.5 |
| P. fluorescens 63-49 | 25.9 | 8.9 |
| P. fluorescens 34-13 | 22.1 | 10.2 |
| P. putida GR19-1 | 15.1 | −0.1 |
| P. fluorescens 36-43 | 12.2 | 2.2 |
| P. fluorescens 34-36 | −1.2 | 5.0 |

DOCUMENTS CITED IN SPECIFICATION (1) Brown, "Seed and Root Bacterization" *Ann. Rev. Phytopathol,* 12:181–97 (1974).
(2) Harari, "The Involvement of Auzin in the Interaction Between Azospirillum spp. and Grass Roots" (1985 thesis; Hebrew University of Jerusalem).
(3) Kapulnik et al, "Changes in Root Morphology of Wheat Caused by Azospirillum Inoculation," *Can. J. Microbiol.* 31:881–87 (1985).
(4) Kapulnik et al, "Yield Increases in Summer Cereal Crops in Israeli Fields Inoculated with Azospirillum," *Exp'tl. Agricul.* 17:179–87 (1981),
(5) Kloepper et al, "Enhanced Plant Growth by Rhizobacteria," *Nature* 86:885–86 (1980).
(6) Kloepper & Schroth, "Plant Growth-Promoting Rhizobacteria and Plant Growth Under Gnotobiotic Conditions," *Phytopathol.* 71: 642–44 (1981).
(7) Lifshitz et al, "Nitrogen-Fixing Pseudomonads Isolated from Roots of Plants Grown in the Canadian High Arctic," *Appl. Environ. Microbiol.* 51:251–55 (1986).
(8) Reynlers & Vlassak, "Use of *Azospirillum brasilense* as Biofertilizer in Intensive Wheat Cropping," *Plant & Soil* 66:217–23 (1982).
(9) Scher et al, "Chemotaxis of Fluorescent Pseudomonas spp. to Soybean Seed Exudates In Vitro and In Soil," *Can J. Microbiol.* 31:570–74 (1985).
(10) Scher et al, "A Method for Assessing the Root-Colonizing Capacity of Bacteria on Maize," *Can. J. Microbiol.* 30:151–57 (1984).
(11) Van De Geijn et al, "A Fast Screening Method for Bacterial Isolates Producing Substances Affecting Root-Growth" (presentation to 30th Meeting of the Societe Francaise de Phytopathologie, 14–17 April 1986 ).

What is claimed is:

1. A biologically pure bacterial culture of at least one strain of a bacteria that is root-colonizing and that directly promotes plant development, wherein said strain: (i) promotes plant growth under gnotobiotic conditions, and (ii) has substantially all of the plant growth characteristics of *Pseudomonas putida* GR 12-2, deposited under ATCC accession No. 53,555, and variants thereof wherein said variants retain said characteristics.

2. A bacterial culture according to claim 1, wherein said strain is a fluorescent pseudomonad.

3. A bacterial culture according to claim 2, wherein said strain is an arctic-diazotrophic pseudomonad.

4. A bacterial culture according to claim 3, wherein said strain is selected from the group consisting of *Pseudomonas putida* GR12-2, deposited under ATCC accession No. 53,555 and mutations thereof.

5. A bacterial culture according to claim 1, wherein said strain is of a species selected from the group consisting of *Pseudomonas putida, Pseudomonas fluorescens* and *Serratia liquefaciens.*

6. A bacterial culture according to claim 1, wherein said strain promotes phosphorus uptake in a plant.

7. A bacterial culture according to claim 1, wherein said strain promotes development in rape plants.

8. A composition of matter comprising (i) a biologically pure bacterial culture of a strain of bacteria that is root-colonizing and directly promotes plant development and (ii) a synthetic agriculturally-compatible carrier, wherein said strain: (i) promotes plant growth under gnotobiotic conditions, and (ii) has substantially all of the plant growth characteristics of *Pseudomonas putida* GR 12-2, deposited under ATCC accession No. 53,555, and variants thereof wherein said variants retain said characteristics.

9. A composition according to claim 8, wherein said composition consists essentially of said strain and said carrier.

10. A composition according to claim 8, wherein said strain is a fluorescent pseudomonad.

11. A composition according to claim 10, wherein said strain is an arctic-diazotrophic pseudomonad.

12. A composition according to claim 11, wherein said strain is selected form the group consisting of *Pseudomonas putida* GR12-2, deposited under ATCC accession No. 53,555, and mutations thereof.

13. A composition according to claim 8, wherein said strain is of a species selected from the group consisting of *Pseudomonas putida, Pseudomonas fluorescens* and *Serratia liquefaciens.*

14. A composition according to claim 8, wherein said strain promotes phosphorus uptake in a plant.

15. A composition according to claim 8, wherein said strain promotes development in rape plants.

16. A composition according to claim 8, wherein bacterial cells of said strain are suspended in a carrier which comprises a liquid.

17. A composition according to claim 16, wherein said carrier is an aqueous liquid.

18. A composition according to claim 17, further comprising an alginate.

19. A composition according to claim 18, further comprising an agriculturally compatible oil, such that said composition is an emulsion containing bacterial cells of said strain.

20. A composition according to claim 16, wherein said carrier comprises an agriculturally compatible oil.

21. A composition according to claim 20, further comprising a gum in an amount such that said composition is an emulsion in which said bacterial cells of said strain are dispersed.

22. A composition according to claim 16, wherein said carrier further comprises a granular material onto which said liquid is absorbed.

23. A composition according to claim 22, wherein said granular material comprises pelleted peat or perlite granules.

24. A composition according to claim 8, wherein said composition is the product of a process comprising the steps of (a) dispersing bacterial cells of said strain in an aqueous slurry and (b) drying said slurry to powder at a temperature which does not adversely affect said cells.

25. A composition according to claim 24, wherein said process further comprises the step of mixing said powder with material selected from peat, talc and diatomaceous earth.

26. A composition according to claim 24, wherein said process further comprises the step of mixing said powder in an agriculturally compatible oil.

27. A method for promoting development of a plant, comprising the step of exposing seed from which said plant is grown to a composition of matter comprising (i) a biologically pure bacterial culture of a strain of bacteria that is root-colonizing and directly promotes plant development and (ii) a Synthetic agriculturally-compatible carrier, wherein said strain: (i) promotes plant growth under gnotobiotic conditions, and (ii) has substantially all of the plant growth characteristics of *Pseudomonas putida* GR 12-2, deposited under ATCC accession No. 53,555, and variants thereof wherein said variants retain said characteristics.

28. A method according to claim 27, further comprising the step of growing said seed under conditions such that competition between said strain (i) and indigenous microbes plays substantially no role in promotion of plant development by said strain (i).

29. A seed product produced by a process as claimed in claim 27.

30. A seed product according to claim 29, wherein said strain is a fluorescent pseudomonad.

31. A seed product according to claim 30, wherein said strain is an arctic-diazotrophic pseudomonad.

32. A seed product according to claim 31, wherein said strain is selected from the group consisting of *Pseudomonas putida* GR12-2, deposited under ATCC accession No. 53,555 and mutations thereof.

33. A seed product according to claim 29, wherein said strain is of a species selected from the group consisting of *Pseudomonas putida, Pseudomonas fluorescens* and *Serratia liquefaciens*.

34. A seed product according to claim 29, wherein said strain promotes phosphorus uptake in a plant.

35. A seed product according to claim 29, wherein said strain promotes development in rape plants.

36. A method for obtaining a bacterial strain that directly promote plant development, comprising the steps of:

assessing the ability of a bacterial strain directly to promote growth of a plant by applying the root-colonizing bacterial strain under gnotobiotic conditions to the growth environment of the plant; and maintaining a culture of the bacterial strain if it has substantially all of the plant growth characteristics of *Pseudomonas putida* GR 12-2, deposited under ATCC accession No. 53,555, and variants thereof wherein said variants retain said characteristics.

37. A method according to claim 36, wherein the bacterial strain is additionally tested for root-colonizing ability.

38. A method according to claim 36, wherein the bacterial strain to be tested for the ability directly to promote growth is isolated from soil.

39. A method according to claim 36, wherein the step of assessing the ability of bacterial strain directly to promote growth comprises applying the bacterial strain to a seed of the plant and planting the seed under gnotobiotic conditions.

40. A biologically pure bacterial culture of a rhizobacterial strain selected from the group consisting of *Pseudomonas putida, Pseudomonas fluorescens,* and *Serratia liquifaciens* that directly promotes growth of plants that is identified according to the method recited in claim 36.

* * * * *